(12) United States Patent
Bogedain et al.

(10) Patent No.: US 6,541,012 B2
(45) Date of Patent: Apr. 1, 2003

(54) SYSTEM FOR THE PRODUCTION OF AAV VECTORS

(76) Inventors: Christoph Bogedain, Gabelsberger Strasse 48c, D-80333 Munich (DE); Gerd Maass, Mitterweg 17, D-82402 Sindelsdorf (DE); Michael Hallek, Brunnenstr. 40, D-86938 Schondorf (DE)

( * ) Notice: Subject to any disclaimer, the term of this patent is extended or adjusted under 35 U.S.C. 154(b) by 0 days.

(21) Appl. No.: 09/908,660

(22) Filed: Jul. 18, 2001

(65) Prior Publication Data

US 2002/0081709 A1 Jun. 27, 2002

Related U.S. Application Data

(62) Division of application No. 09/214,151, filed as application No. PCT/DE97/01333 on Jun. 24, 1997, now Pat. No. 6,294,370.

(30) Foreign Application Priority Data

Jun. 24, 1996 (DE) .......................... 196 25 188

(51) Int. Cl.[7] .................. A61K 39/23; A61K 39/12; C07H 21/04
(52) U.S. Cl. ................. 424/233.1; 424/199.1; 424/204.1; 536/23.72; 536/23.4
(58) Field of Search ........... 424/199.1, 204.1, 424/233.1; 536/23.72, 23.4

(56) References Cited

U.S. PATENT DOCUMENTS 5,856,152 A  1/1999  Wilson et al. ............ 435/172.3

FOREIGN PATENT DOCUMENTS

| EP | 0 797 678 B1 | 3/2001 |
| WO | WO 95/13392 | 5/1995 |
| WO | WO 95/34670 | 12/1995 |
| WO | WO 96/17947 | 6/1996 |

OTHER PUBLICATIONS

Bett et al., 1994, "An efficient and flexible system for construction of adenovirus vectors with insertions or deletions in early regions 1 and 3," *Proc. Natl. Acad. Sci. U.S.A.* 91:8802–8806.
Bett et al., 1995 "DNA sequence of the deletion/insertion in early region 3 of Ad5 dl309," *Virus Res.* 39:75–82.
Chiorini et al., 1995, "High–Efficiency Tranfer of the T Cell Co–Stimulatory Molecule B7–2 to Lymphoid Cells Using High–Titer Recombinant Adeno–Associated Virus Vectors," *Human Gene Therapy* 6:1531–1541.
Flotte et al., 1995, "An improved system for packaging recombinant adeno–associated virus vectors capable of in vivo transduction," *Gene Therapy* 2:29–37.
Logan and Shenk, 1984, "Adenovirus tripartite leader sequence enhances translationof mRNAs late after infection," *Proc. Natl. Acad. Sci. U.S.A.* 81:3655–3659.
Maass et al., 1998, "Recombinant Adeno–Associated Virus for the Generation of Autologous, Gene–Modified Tumor Vaccines: Evidence for a High Transduction Efficiency into Primary Epithelial Cancer Cells," *Human Gene Therapy* 9:1049–1059.

*Primary Examiner*—Hankyel T. Park

(57) ABSTRACT

The invention concerns a system comprising an AAV vector, which contains a foreign DNA, and rep 68/78 sequences of AAV with delayed expression, these sequences being present (a) in cis or (b) in trans. The invention also concerns the use of such a system for the production of AAV vectors.

11 Claims, No Drawings

SYSTEM FOR THE PRODUCTION OF AAV VECTORS

This is a division of application Ser. No. 09/214,151 filed Aug. 6, 1999, now U.S. Pat. No. 6,294,370, which is a 371 of PCT/DE97/01333, filed Jun. 24, 1997.

This is a national phase filing of the Application No. PCT/DE97/01333, which was filed with the Patent Corporation Treaty on Jun. 24, 1997, and is entitled to priority of the German Patent Application P 196 25 188.5, filed Jun. 24, 1996.

I. FIELD OF THE INVENTION

The present invention relates to a system suitable for the production of AAV vectors, and its use.

II. BACKGROUND OF THE INVENTION

For carrying out gene-therapeutic measures it is important to have vectors which can introduce foreign genes into the genomes of cells and which are not toxic for them. An example of such vectors are adeno-associated viruses (AAVs).

AAVs are single-stranded DNA viruses belonging to the parvovirus family. AAVs need helper viruses, particularly adenoviruses or herpesviruses, for their replication. In the absence of helper viruses, AAVs integrate into the host cell genome, particularly at a specific site of chromosome 19.

The genome of AAVs is linear and has a length of about 4680 nucleotides. It comprises two reading frames which code for a structural gene and a non-structural gene. The structural gene is referred to as cap gene. It is controlled by the P40 promoter and codes for three capsid proteins. The non-structural gene is referred to as rep gene and codes for the Rep proteins, Rep 78, Rep 68, Rep 52 and Rep 40. The two former proteins are expressed under the control of the P5 promoter while the expression of Rep 52 and Rep 40 is controlled by the P19 promoter. The functions of the Rep proteins are represented inter alia by the control of the replication and transcription of the AAV genome.

However, the production of AAVs is extremely problematic. In particular, it is difficult to prepare great amounts of recombinant AAVs (rAAVs), i.e., AAVs containing a foreign DNA. Even the attempt of using adenoviruses as vectors for rAAVs does not yield satisfactory results.

Therefore, it is the object of the present invention to provide a product by which rAAVs can be provided in great amounts.

III. SUMMARY OF THE INVENTION

The invention concerns a system comprising an AAV vector, which contains a foreign DNA, and rep 68/78 sequences of AAV with delayed expression, these sequences being present (a) in cis or (b) in trans.

The invention also concerns the use of such a system for the production of AAV vectors.

IV. DETAILED DESCRIPTION OF THE INVENTION

It is the object of the present invention to provide a product by which rAAVs can be provided in great amounts. According to the invention this is achieved by the subject matters defined in the claims.

Thus, the subject matter of the present invention relates to a system comprising an AAV vector containing a foreign DNA and rep 68/78 sequences of AAV whose expression regarding the DNA replication of the AAV vector or of part thereof is delayed, the rep 68/78 sequences being present (a) in cis or (b) in trans.

The present invention is based on the applicant's discovery that the Rep proteins 68 and 78 of AAV impair the replication of AAV DNA and that this impairment can be prevented by a delayed expression of the sequences encoding the Rep proteins 68 and 78.

The expression "AAV vector" refers to any AAV vector which contains no rep 68/78 sequences of AAV expressed in non-delayed fashion regarding the DNA replication of the AAV vector or of part thereof. The expression "part of the AAV vector" relates to any part of the AAV vector, particularly its cap sequences and the sequences coding for the Rep proteins 40 and 52.

The expression "rep 68/78 sequences of AAV" refers to the fact that the system according to the invention comprises rep 68 sequences and/or rep 78 sequences of AAV whose expression regarding the DNA replication of the AAV vector or of part thereof is delayed.

The expression "foreign DNA" comprises any foreign DNA which may be integrated in an above AAV vector. The foreign DNA can be non-coding or coding. In the former case, the foreign DNA may be a regulator or control element of DNA replication and/or transcription. In the latter case, it is favorable for the foreign DNA to be expressible, it being particularly advantageous for the expression to be controlled by a constitutive or inducible promoter such as a tissue-specific or tumor-specific promoter. In addition, the foreign DNA may code for a diagnostic and/or therapeutic protein. Examples of a therapeutic protein are tumor necrosis factor, interferons, interleukins, lymphokines, growth factors, plasma proteins such as coagulation factors and metabolic enzymes, and receptors. In particular, the foreign DNA may code for proteins which can increase the immunogenicity of cells. These may be proteins which are lacking tumor cells, e.g., cytokines, such as IL-2, interferons and GM-CSF, and costimulatory molecules, such as B7-1 tumor-associated antigens, e.g., MAGE1, tyrosinases, lymphone-specific idiotypes and viral proteins, e.g., E7 protein of human papilloma virus and EBNA 3 protein of Epstein-Barr virus. The foreign DNA may be integrated at any site of the AAV vector. It may be favorable for several foreign DNAs to be present in one AAV vector.

A system according to the invention comprises in (a) an AAV vector and in cis, i.e., on the AAV vector, the present rep 68/78 sequences of AAV, which are expressed in delayed fashion regarding the DNA replication of the AAV vector or of part thereof. Such an AAV vector can be obtained by common methods. It is favorable to use as a basis an AAV vector which has a DNA coding for Rep proteins of AAV. The endogenic P5 promoter of the rep 68 and rep 78 sequences of AAV can be replaced in such an AAV vector by one which is active after the DNA replication of the AAV vector or of part thereof. Such a promoter is e.g., the "major late promoter" of adenovirus or a derivative thereof. An inducible promoter, e.g., the metallothioneine promoter or a derivative thereof, can also be used in place of the endogenic P5 promoter of the rep 68 and rep 78 sequences of AAV.

In a preferred embodiment the AAV vector is present in (a) in a product (I), which may be any product that does not impair the functionality of the AAV vector, particularly its replication. Product (I) is favorably a vector, e.g., a virus or plasmid vector, or a cell.

A system according to the invention comprises in (b) an AAV vector and in trans, i.e. separated from the AAV vector, the present rep 68/78 sequences of AAV which are expressed in delayed fashion regarding the DNA replication of the AAV vector or of part thereof. The rep 68/78 sequences of AAV are preferably present in a product (II). It can be any product which does not impair the functionality of the rep 68/78 sequences of AAV, particularly their delayed expression. The latter can be obtained as described in (a) A product (II) is advantageously a vector, e.g., a virus or plasmid vector, or a cell.

It will be particularly favorable if, in (b), the AAV vector is present in a product (I) and the rep 68/78 sequences of AAV are present in a product (II). Products (I) and (II) may have the above meanings, but cannot be cells at the same time. It is advantageous for products (I) and (II) to be virus vectors, e.g., adenovirus vectors or a combination of adenovirus and vaccinia virus vectors. It is particularly favorable for the virus vectors to complement one another. Virus vectors are described below as products (I) and (II). This has to be considered by way of example.

Product (I) is an adenovirus vector which in place of the E1 sequences of adenovirus contains an AAV vector having ITR sequences of AAV and a foreign DNA.

Product (II) is an adenovirus vector which in place of the E3 sequences of adenovirus contains rep and cap sequences of AAV, the rep 68/78 sequences of AAV being controlled by a promoter active after the DNA replication of the AAV vector or of part thereof, e.g., the "major late promoter" of adenovirus, the rep 40 and rep 52 sequences of AAV being controlled by the endogenic p19 promoter, and the cap sequences of AAV being controlled by a constitutive promoter, e.g., the CMV promoter; product (II) is a combination of two adenovirus vectors, one of which contains rep sequences of AAV in place of the E3 sequences of adenovirus, the rep 68/78 sequences of AAV being controlled by the "major late promoter" of adenovirus and the rep 40 and rep 52 sequences of AAV being controlled by the endogenic p19 promoter, and the other contains cap sequences of AAV which are controlled by the CMV promoter, in place of the E4 sequences of adenovirus; product (II) is a combination of an adenovirus vector and a vaccinia virus vector, the former containing, in place of the E3 sequences of adenovirus, rep 40 and rep 52 sequences of AAV under the control of the endogenic p19 promoter and cap sequences of AAV under the control of the CMV promoter, and the latter containing rep 68/78 sequences of AAV. The vaccinia virus vector is not added until the DNA replication of the adenovirus vectors is fully or partially complete.

A system according to the invention is suited to prepare recombinant AAVs (rAAVs) in great amounts. For this purpose, the system according to the invention is introduced into cells which permit the replication of rAAVs. These are e.g. 293 cells. The cells are then infected with helper viruses such as adenoviruses. This may be omitted if the system according to the invention provides all elements necessary for the replication of rAAVs. This is found particularly when the system according to the invention is present in alternative (b) in which products (I) and (II) are virus vectors, particularly adenovirus vectors or a combination of adenovirus and vaccinia virus vectors, which complement one another. The complementation may also be given if one of the products is a virus vector and the other product is a cell providing the protein whose DNA is deleted in the virus vector.

By means of the present invention it is possible to provide rAAVs which can be used for diagnostic and/or therapeutic measures. Such measures can be taken in well-calculated fashion by selecting the foreign DNA.

The below examples explain the invention in more detail. The following preparations and examples are given to enable those skilled in the art to more clearly understand and to practice the present invention. The present invention, however, is not limited in scope by the exemplified embodiments, which are intended as illustrations of single aspects of the invention only, and methods which are functionally equivalent are within the scope of the invention. Indeed, various modifications of the invention in addition to those described herein will become apparent to those skilled in the art from the foregoing description and accompanying drawings. Such modifications are intended to fall within the scope of the appended claims.

V. EXAMPLES

A. Example 1

Preparation of a System According to the Invention
(a) Preparation of a Recombinant Adenovirus Into Which rep/cap Sequences of AAV (rep/cap Expression Cassette) are Integrated in the E1 Region of the Adenoviral Genome.

Reference is made to the method by Bett et al., 1994, Proc. Natl. Acad. Sci. U.S.A . 91:8802–8806. Rep 68/78 sequences of AAV are controlled by the "major late promoter" to achieve delayed expression. Rep 40/52 sequences of AAV remain under the control of the endogenic p19 promoter. Cap sequences of AAV are controlled by the CMV promoter. Furthermore, the cap sequences in the 5'-untranslated region of the mRNAs contain sequences from the 5'-untranslated region of the subsequent adenoviral mRNAs.

Production of a Rep/Cap Expression Cassette

A partial sequence of the rep gene (positions 1882 to 2280) is amplified by PCR using primers 5'-CGCCGGAAGCTTCGATCAACTACGCAGACAG- 3' (SEQ ID NO:1) and 5'-GCGGGCGTCGACTTTGAGCTTC CACCACTGTCTTAT -3' (SEQ ID NO:2) from a matrix containing the AAV genome (e.g., pSVOriAAV), excised using HindIII/SalI and inserted in plasmid pUC19 excised with the same enzymes. pUC19RepdupI is obtained. The cDNA sequence of the 5'-untranslated leaders of the subsequent adenovirus mRNAs is amplified by PCR using the primers 5'-CGGGGTACCCAGCTGACTCTCTTCCGCA TCGCTG-3' (SEQ ID NO:3) and 5'-CGCGGATCCG AATTCAAGCTTCTCGAGAGGTTTTCCGATC-3' (SEQ ID NO:4) from plasmid pMPCV2 (Logan and Shenk, 1984, Proc. Natl. Acad. Sci. U.S.A. 81:3655–3659), flanking restriction sites fitting for further clonings forming. The amplificate is excised using KpnI/BamHI and inserted in plasmid pCEP4 excised with the same enzymes (Invitrogen company), the vector pCEP4-CMVL forming. The CMV promoter is excised, together with the leader, from the pCEP4-CMV leader using EcoRI/SalI and inserted in the pUC19RepdupI linearized by means of the same restriction enzymes. pRepdupI-CMVL forms. The region including the rep partial sequence and the CMV promoter and the adeno leader is excised from the resulting pRepdupI-CMV leader using HindIII and inserted in partially HindIII-excised pSVOriAAV (Chiorini et al., 1995, J. Virol. 69:7334–7338). pRepCMVLCap forms. The insertion in the appropriate place and in the appropriate orientation is checked by means of adequate restriction cleavages.

By this procedure the CMV promoter is inserted in pRepCMVLCap between the rep and cap sequences, the interruption of the rep reading frame being prevented by the duplication of a partial sequence and the CMV promoter being inserted in the HindIII restriction site at position 1883 of the AAV sequence of the pSVOriAAV. This HindIII restriction site is located between the transcription startpoint of the p40 promoter and the 5'-splicing signal of the cap sequences.

pRepCMVLCap is linearize using SpeI and treated with T4 exonuclease. A time series of the T4 exonuclease treatment enables the formation of various sizes of the deleted region. A construct is used for further processing, in which the 5' region of the AAV genome is deleted up to a point between positions 288 and 321, so that the remaining sequence begins between the transcription start of the rep68/78 sequences, position 288, and the start codon of these sequences, position 321. A polylinker sequence with XbaI, NotI, SpeI, and BglII restriction sites is inserted in the deleted region by synthetic linkers, so that pRepCMVLCap forms. The major late promoter is amplified using the forms. The major late promoter is amplified using the primers 5'-CGTCTAGAGCGGCCGCCCGCGGTCCTCCTCGTA TAGAAACT-3' (SEQ ID NO:5) and 5'-GCAGATCTAC TAGTCTCGAGAGGTTTTCCGATCCGGTCG-3' (SEQ ID NO:6) from pMPCV2 (Logan and Shenk, 1984, supra) and subsequently excised using BglII/XbaI. pRepCMVL-Cap* is excised using BglII/XbaI and the major late promoter is inserted in the proper orientation, so that pML-PRepCMVLCap forms.

The rep cassette has the endogenous p19 promoter which is embedded in the rep sequence and further controls the expression of the proteins rep4o and rep52, whereas only the sequences for rep68/78 are controlled by the major later promoter.

Preparation of a Recombinant Adenovirus having Rep/Cap Expression Cassette

The rep/cap expression cassette is excised from pML-PRepCMVLCap using XbaI/ClaI and inserted in the vector pΔE1sp1A linearize with the same enzymes (Bett et al., 1995, Virus Res. 39:75–82). This plasmid contains the sequences of the adenovirus type 5 between map units 0 and 0.9 as well as 9.8 and 15.8, the E1A region having been substituted by a polylinker sequence for the insertion of foreign genes.

Genomes of infectious recombinant adenoviruses may form by in vivo recombination between overlapping regions of adenoviral sequences on pBHG10, which contains the adenovirus sequences between map units 0 and 0.5, from 3.7 to 78.3 and from 85.8 to 100, as well as the pΔE1sp1A derivative which contains rep/cap sequences. The co-transfection of the two plamids in 293 cells is carried out to complement the E1A gene. A cytopathic effect which manifests itself several days after the transfection, signifies the formation of recombinant adenoviruses. The 293 cells which show a cytopathic effect, are broken up by freezing and thawing and recombinant viruses (Adrep/cap) are isolated from the lysate by double plaque purification. Individual clones are amplified by successive passage over 293 cultures. The expression patterns of rep and cap are characterized by Western blotting.

(b) Preparation of a Recombinant Adenovirus into which an rAAV Genome is Integrated A foreign DNA, e.g. a luciferase reporter gene having flanking AAV ITR sequences, is integrated into the E1A region of an adenovirus. The expression cassette with the ITR sequences is excised using PvuII from the vector pAAVCMVLuc (cf. Maass et al.), which contains the luciferase reporter gene under the control of the CMV promoter, flanked by AAV ITR sequences in a pEMBL8 vector. This fragment is integrated within EcoRV-excised pΔE1sp1A over the blunt ends. pΔE1sp1A-Luc forms. The recombinant adenoviruses (AdAALuc) are prepared by co-transfection of pΔE15p1A-Luc and pBHG10 in 293 cells by in vivo recombination, as described in (a).

(c) Production of Recombinant AAV Vectors by Infection of 293 Cells with Adrep/cap and AdAAVLuc 4×10$^8$ 293 cells are cultured to give 80% confluence and with a m.o.i. of 10 each simultaneously infected with Adrep/cap and AdAAV-Luc in a small volume or serum-free medium. Full medium is added 2 hours after the infection. 3 days after the infection, the cells are removed with a cell scraper from the surface of the culture vessels; the suspension is centrifuged off at 200 g and room temperature for 5 min. The cell pellets are suspended in 28 ml TD buffer (140 mM NaCl, 5 mM KCl, 0.7 mM K$_2$HPO$_4$, 25 mM Tris/Cl, pH 7.4), and 2 ml 10% (w/v) sodium deoxycholate and 2 ml 0.25% trypsin solution are added. To break up cells, the lysate is incubated at 37° C. for 30 min. and then treated with a Dounce homogenizer. A density of 1.4 g/ml is adjusted with CsCl, and the lysate is subjected to an isopycnic density gradient centrifugation at 130,000 g and 29° C. for 24 h. Fractions having a refractory index between 1.3705 and 1.3750 are collected with a collecting rap, combined and subjected to another density gradient centrifugation under equal conditions. Fractions having a refractory index between 1.3705 and 1.3750 are collected again and dialyzed against 0.9% NaCl solution. The resulting AAV lyzate can be used in biological tests, e.g. a luciferase expression test.

All references cited within the body of the instant specification are hereby incorporated by reference in their entirety.

What is claimed:

1. A vector comprising rep68/78 sequences of AAV with delayed expression.

2. The vector of claim 1, wherein the vector construct is a virus vector.

3. The vector of claim 1, wherein the vector construct is an adenovirus vector.

4. The vector of claim 1, wherein the vector construct is a combination of adenovirus and vaccinia virus vector.

5. The vector of claim 1, wherein the expression of the rep68/78 sequences of AAV is controlled by a promoter active after the DNA replication of the AAV vector.

6. The vector of claim 5, wherein the promoter is the major late promoter of adenovirus.

7. The vector of claim 5 or 6, wherein the promoter is active after the replication of part of the DNA of the AAV vector.

8. The vector of claim 1, wherein the rep68/78 sequences of AAV are integrated into one of the early genes of adenovirus.

9. The vector of claim 1, wherein the rep68/78 sequences of AAV are integrated into one of the late genes of adenovirus.

10. The vector of claim 1, wherein the vector additionally comprises sequences selected from the group consisting of sequences coding for rep40, rep52 and/or cap.

11. The vector of claim 1, wherein the vector additionally comprises an AAV vector having ITR sequences of AAV and a foreign DNA.

* * * * *

SEQUENCE LISTING

<160> NUMBER OF SEQ ID NOS: 6

<210> SEQ ID NO 1
<211> LENGTH: 31
<212> TYPE: DNA
<213> ORGANISM: Artificial Sequence
<220> FEATURE:
<223> OTHER INFORMATION: Primer

<400> SEQUENCE: 1
cgccggaagc ttcgatcaac tacgcagaca g        31

-continued

<210> SEQ ID NO 2
<211> LENGTH: 36
<212> TYPE: DNA
<213> ORGANISM: Artificial Sequence
<220> FEATURE:
<223> OTHER INFORMATION: Primer

<400> SEQUENCE: 2
gcgggcgtcg actttgagct tccaccactg tcttat                          36

<210> SEQ ID NO 3
<211> LENGTH: 34
<212> TYPE: DNA
<213> ORGANISM: Artificial Sequence
<220> FEATURE:
<223> OTHER INFORMATION: Primer

<400> SEQUENCE: 3
cggggtaccc agctgactct cttccgcatc gctg                            34

<210> SEQ ID NO 4
<211> LENGTH: 40
<212> TYPE: DNA
<213> ORGANISM: Artificial Sequence
<220> FEATURE:
<223> OTHER INFORMATION: Primer

<400> SEQUENCE: 4
cgcggatccg aattcaagct tctcgagagg ttttccgatc                      40

<210> SEQ ID NO 5
<211> LENGTH: 41
<212> TYPE: DNA
<213> ORGANISM: Artificial Sequence
<220> FEATURE:
<223> OTHER INFORMATION: Primer

<400> SEQUENCE: 5
cgtctagagc ggccgcccgc ggtcctcctc gtatagaaac t                    41

<210> SEQ ID NO 6
<211> LENGTH: 39
<212> TYPE: DNA
<213> ORGANISM: Artificial Sequence
<220> FEATURE:
<223> OTHER INFORMATION: Primer

<400> SEQUENCE: 6
gcagatctac tagtctcgag aggttttccg atccggtcg                       39